US012622703B2

(12) United States Patent
Watson

(10) Patent No.: US 12,622,703 B2
(45) Date of Patent: May 12, 2026

(54) COILS USED IN INTRAVASCULAR TREATMENT

(71) Applicant: David A. Watson, San Jose, CA (US)

(72) Inventor: David A. Watson, San Jose, CA (US)

( * ) Notice: Subject to any disclaimer, the term of this patent is extended or adjusted under 35 U.S.C. 154(b) by 247 days.

(21) Appl. No.: 18/202,223

(22) Filed: May 25, 2023

(65) Prior Publication Data

US 2023/0380842 A1 Nov. 30, 2023

Related U.S. Application Data

(60) Provisional application No. 63/346,775, filed on May 27, 2022.

(51) Int. Cl.
*A61B 17/12* (2006.01)
*A61B 17/00* (2006.01)

(52) U.S. Cl.
CPC .. *A61B 17/12145* (2013.01); *A61B 17/12113* (2013.01); *A61B 2017/00526* (2013.01); *A61B 2017/00867* (2013.01)

(58) Field of Classification Search
CPC ........ A61B 17/12145; A61B 17/12113; A61B 2017/00526; A61B 2017/00867
See application file for complete search history.

(56) References Cited

U.S. PATENT DOCUMENTS 5,639,277 A 6/1997 Mariant et al.
8,801,747 B2 * 8/2014 Strauss ............ A61B 17/12022
606/200

9,414,819 B2 8/2016 Fitz et al.
9,717,502 B2 8/2017 Teoh et al.
9,775,620 B2 10/2017 Teoh et al.
(Continued)

FOREIGN PATENT DOCUMENTS

DE 10341938 A1 4/2005
EP 2859854 B1 9/2009
(Continued)

OTHER PUBLICATIONS

Supplementary European Search Report, EP23812650, Oct. 22, 2024, 10 pages.
(Continued)

*Primary Examiner* — Kathleen S Holwerda
*Assistant Examiner* — James R McGinnity
(74) *Attorney, Agent, or Firm* — Edell, Shapiro & Finnan, LLC

(57) ABSTRACT

A complex coil for intravascular treatment, a mandrel for constructing the complex coil, and the method for constructing the complex coil is disclosed. The coil generally comprises a primary wire formed to a primary spring and then formed to a secondary three dimensional shape, wherein the primary spring forms a secondary set of layers of successive loops. A fixed number of loops define a layer forming a locus of points enclosing a generally spherical surface and forming a repeatable pattern, the second successive layer of loops of the repeatable pattern being generally larger in diameter and spherical size than the previous layer. The locus of the points from the four or more loops define an enclosed spheroid adapted to fill or frame an embolism wherein the size and geometry of the successive loops can be manipulated by various means of the unique design of the mandrel.

7 Claims, 10 Drawing Sheets

(56)                References Cited

U.S. PATENT DOCUMENTS

| | | | |
|---|---|---|---|
| 9,855,050 | B2 | 1/2018 | Lorenzo et al. |
| 10,537,333 | B2 | 1/2020 | Teoh et al. |
| 11,357,513 | B2 | 6/2022 | Bowman et al. |
| 11,622,772 | B2 | 4/2023 | Teoh et al. |
| 11,707,281 | B2 | 7/2023 | Fitz et al. |
| 12,035,918 | B2 | 7/2024 | Bowman |
| 2005/0192618 | A1 | 9/2005 | Porter |
| 2005/0192619 | A1 | 9/2005 | Teoh et al. |
| 2006/0100661 | A1 | 5/2006 | Jaeger et al. |
| 2007/0055302 | A1 | 3/2007 | Henry et al. |
| 2007/0175536 | A1 | 8/2007 | Monetti et al. |
| 2008/0228215 | A1 | 9/2008 | Strauss et al. |
| 2008/0319532 | A1 | 12/2008 | Monstadt et al. |
| 2009/0254112 | A1 | 10/2009 | Gorospe et al. |
| 2009/0264914 | A1 | 10/2009 | Riina et al. |
| 2012/0232356 | A1 | 9/2012 | Coelho |
| 2013/0018409 | A1 | 1/2013 | Le et al. |
| 2013/0184658 | A1 | 7/2013 | Duncan |
| 2014/0277095 | A1 | 9/2014 | Kerr |
| 2015/0057700 | A1 | 2/2015 | Chen et al. |
| 2015/0182226 | A1 | 7/2015 | Teoh |
| 2015/0238198 | A1 | 8/2015 | Le et al. |
| 2015/0289881 | A1 | 10/2015 | Suzuki et al. |
| 2017/0105738 | A1 | 4/2017 | Suzuki |
| 2017/0224350 | A1 | 8/2017 | Shimizu et al. |
| 2018/0021834 | A1 | 1/2018 | Suzuki |
| 2018/0263630 | A1 | 9/2018 | Tsukumo |
| 2019/0015107 | A1* | 1/2019 | Dias .................. A61B 17/1214 |
| 2019/0142436 | A1 | 5/2019 | Koyama et al. |
| 2019/0298387 | A1 | 10/2019 | Qin et al. |
| 2020/0187951 | A1 | 6/2020 | Blumenstyk |
| 2020/0352576 | A1 | 11/2020 | Wu |
| 2021/0000480 | A1 | 1/2021 | Ikuno et al. |
| 2021/0085334 | A1 | 3/2021 | To et al. |
| 2021/0137526 | A1 | 5/2021 | Lee et al. |
| 2021/0338249 | A1* | 11/2021 | Guo ................. A61B 17/12145 |
| 2023/0329720 | A1 | 10/2023 | Delgadillo et al. |

FOREIGN PATENT DOCUMENTS

| | | |
|---|---|---|
| EP | 1791590 B1 | 7/2015 |
| EP | 3009084 B1 | 9/2017 |
| EP | 2558000 B1 | 9/2019 |
| EP | 4151164 A1 | 3/2023 |
| WO | 23091852 A1 | 5/2023 |

OTHER PUBLICATIONS

International Preliminary Report on Patentability and the Written Opinion, PCT/US2023/2023743, Nov. 7, 2024, 5 pages.

* cited by examiner

740

750

COILS USED IN INTRAVASCULAR TREATMENT

CROSS-REFERENCES TO RELATED APPLICATIONS

This application claims priority to U.S. Provisional Patent Application No. 63/346,775, filed May 27, 2022, the content of which is incorporated by reference herein in its entirety.

BACKGROUND

The present invention relates generally to implantable devices for interventional therapeutic treatment and vascular surgery, and more particularly to a therapeutic device in the form of an embolic or vasoocclusive coil deployable within a patient's vasculature, and a mandrel for making a novel coil structure.

The art and science of interventional therapy and surgery has continually progressed in the treatment of vascular defects and diseases by the use of ever smaller incisions or access through the vasculature or body openings in order to reduce the trauma to tissue surrounding the treatment site. One important aspect of such treatments involves the use of catheters to place therapeutic devices at a treatment site by access through the vasculature. Examples of such procedures include transluminal angioplasty, placement of stents to reinforce the walls of a blood vessel, and the use of vasoocclusive devices to treat defects or weaknesses in the vasculature.

One specific field of interventional therapy that has been able to advantageously use recent developments in technology is the treatment of neurovascular defects. As smaller and more capable structures and materials are developed, treatment of vascular defects in the human brain that were previously untreatable or presented an unacceptable risk via conventional surgery have become more amenable to treatment thanks to these advances. One type of therapy that has become advantageous for the treatment of defects in the neurovasculature is the catheter placement of vasoocclusive devices such as embolic coils into a damaged portion of a vein or artery.

Vasoocclusive devices are therapeutic devices that form an embolus to block or restrict the flow of blood through a vessel or to prevent blood from entering an aneurysm in the vessel. One such vasoocclusive device widely used for this purpose is a helical wire coil that transforms in a deployed configuration to a three dimensional shape to engage the walls of an aneurism. Vasoocclusive devices are designed to conform with the shape of an aneurysm and are made of a pre-formed strand of material such as a platinum-tungsten alloy. US Patent Publication No. 2009/0297582, the content of which is incorporated herein by reference, describes some examples of materials suitable for embolic coils. These vasoocclusive devices comprise one or more vasoocclusive strands wound in a manner so as to form a generally spherical or ovoid shape in its deployed state. The strand is typically first helically wound in a generally linear fashion, and then wound around an appropriately shaped mandrel, and then heat treated to impart the shape of the mandrel after its removal. Radiopacity may be provided by the natural radiopacity of a platinum alloy wire when so constructed. The coils can take a variety of configurations, and may generally be characterized as either 'framing coils' or 'filling coils.' Framing coils are intended to have a stiffer, more robust shape that approximates the size of the defect (i.e., having the aneurysm's diameter), whereas filling coils tend to be less rigid and function to occupy the spaces left within the voids formed by the previously deployed framing coil(s). In a preferred embodiment of the present invention, a unique mandrel defined herein may be used for creating a framing coil, and also be used to produce a complimentary filling coil with only a minor variation of the technique used in winding the primary strand onto the mandrel.

The delivery of such vasoocclusive devices may be accomplished by a variety of means, including via a catheter whereby the coil device is pushed through the patient's vasculature and deployed in the treatment location. The coil may be releasably attached to the pusher element and a variety of detachment mechanisms are available to release the device from the pusher.

As stated above, aneurysm framing coils are intended to engage aneurysms that may be somewhat spheroid in shape. Framing coils are formed by shaping a primary wind of coil (generally ⅓ to ½ mm in diameter) into a three dimensional pattern that has a mean diameter in some neurovascular applications ranging from about 2 mm to 20 mm. "Framing" refers to the practice where the first coil (and sometimes subsequent coils) is placed inside the aneurysm and the coil is allowed to unfold from its more linear helical configuration on the delivery catheter to a generally spheroidal shape matching the interior of the aneurysm. For this reason, framing coils are designed and specified to treat a specific diameter aneurysm. A ten millimeter framing coil is thus designed to treat an aneurysm having an approximate shape of a ten millimeter diameter sphere, where care is taken to prevent the coil from damaging the weakened tissue at the treatment site.

It is an important feature of embolic coils used for this purpose that the coil unfold and expand in a predictable and consistent manner as it takes its final shape so that the physician can anticipate and control its delivery into the fragile aneurysm or vessel. It is advantageous if the coil(s) unfolds and frames the outer aspects of the aneurysm with the coil having as much surface area in gentle contact with the surface of the aneurysm. When an aneurysm forms on a vessel, the opening in the wall of the vessel at the base of the aneurism is referred to as the neck. It is important that any coil deployed in the aneurism resists falling through the neck and into the parent vessel. The diameter and shape of the loops of the coil can be designed to minimize the opportunity for the coil to escape and enter the parent vessel, the occurrence of which could pose a very sever embolic stroke risk. For example, if a coil had loops that were smaller in diameter than the diameter of the aneurysm neck, the loop could have a very undesirable tendency to deploy outside the neck and into the parent vessel.

In addition to the framing coil, another type of coil is generally referred to as a filling coil. Filling coils are generally deployed after one or more framing coils are in place, and the filling coil is designed to be softer (more flexible) and fill in the voids in the previously deployed (stiffer) framing coil(s). It is well known in the art that aneurisms filled with a higher density of coils tend to heal more efficiently and therefore a device with a higher 'packing density' is desirable. It is therefore beneficial to have filling coils that can easily occupy the spaces left between previously deployed coils within an aneurism to obtain as high a packing density as possible.

SUMMARY OF THE INVENTION

Briefly, and in general terms, the present invention is a therapeutic device for release and deployment within a patient's vasculature that has several unique features not found in the prior art.

Therapeutic coils are typically formed by winding a previously formed linear helical wire spring (referred to as a primary wind) around a form or mandrel and then heating the mandrel and spring to introduce the shape of the mandrel onto the spring (referred to as the secondary shape). Framing coils of the prior art typically use mandrels with round cylindrical posts that generally project from a central hub around which the primary wind is wrapped in a specific pattern.

As the wind is successively wrapped around each post, it is very common for the desired length of the embolic coil to exceed the length required to encircle all the posts of the mandrel. Therefore, to complete the shaping of the coil, the winding of the wire is continued on the cylindrical posts with successive loops being stacked upon the loops that already encircle the post(s). With cylindrical posts, any successive series of loops of the coil will have the same diameter as the previously formed loops on the same post. As the spherical volume of an aneurysm is filled with the coil, and the remaining volume of the aneurysm is diminished by the increased volume of the coils placed before, the available space within the aneurysm diminishes. It is common procedure (referred to as 'nesting') for the attending physician to then select a smaller diameter coil to fit within the previously deployed coils so as to reduce the outward force on the aneurysm wall to reduce the risk of rupture. With cylindrical posts, the successive coils of the same diameter can compete for the same space within the aneurysm and do not nest within each other, thereby potentially reducing the ultimate packing density that can be achieved and potentially increasing outward forces on the aneurysm.

A feature of the present invention is a mandrel with conical or frustoconical shaped coil-forming-posts, wherein the diameter of successive loops wrapped around any post are slightly larger than the previous formed loops on that post. In cases where more than one complete layer of loops define the coil and successive loops are formed on the posts, the so formed coil is loaded onto the pusher mechanism so that it is deployed in the opposite direction to which it was formed. In so doing, with a single embolic coil, the latter deployed series of loops of the coil that form one layer have slightly smaller diameters when compared with the preceding series of loops. This is advantageous because the aneurysm being treated is filled from the outside inwardly and the latter deployed loops (of smaller diameter and reduced spherical radius) more easily fit and fill within the larger previously deployed loops in the reduced volume that is available for the successive loops. The somewhat smaller subsequent loops also provide for a reduced outward force on the fragile aneurism, potentially reducing rupture rates during the procedure. With conventional prior art cylindrical shaped posts, the successive loops are the same diameter as the prior loops and compete with the previously deployed loops to deploy to the same size, thereby potentially adversely increasing outward forces on the aneurysm wall.

Many prior art framing coil mandrels have either four or six cylindrical posts emanating from a central sphere. With a six post configuration, each loop of the coil has a tighter curve/small diameter than with a four post configuration, since the given surface area of a specified sphere is divided amongst six posts instead of four. For a given primary wind, forming such tighter radii loops on the secondary shape causes the coil to be stiffer than a coil having loops with larger radii. Therefore, for this criteria, a four post mandrel configuration has advantages over a six-post configuration. However, with four posts, the larger diameter posts and resulting loops leave a greater surface area between the adjacent posts creating a greater undesirable untreated portion of the aneurysm as compared to the spaces left between six posts. So clearly neither the four or six post configuration is ideal. One prior art coil (U.S. Pat. No. 7,879,064) describes a means to fill in these voids between posts of a four post mandrel with a coil that has smaller loops that are formed within the voids at these vertices. These additional loops would have to be much smaller in diameter and would certainly pose both an embolic risk (for falling from the neck) and would add very stiff sections (as compared to the larger loops of the primary shape) to the embolic coil as it is deployed. Both of these are undesirable features of an embolic coil. One aspect of the present invention capitalizes on the advantages of the four post mandrel, yet solves the problem of the larger untreated intra vertex spaces of four post mandrels without posing an additional embolic risk or stiffening of the coil.

In one embodiment of the present invention, a mandrel is provided employing four posts instead of six cylindrical posts, and therefore has the benefits of the larger the diameters of each loop. However, the mandrel may be formed with posts that are shaped with profiles that are not circular but are rounded triangles, i.e., triangular ellipsoids. When the post geometry is circular, the curvilinear space on the base sphere (corresponding to untreated aneurysm dome) between each adjacent post is significant. When the post geometry is changed from circular to triangular (in the case of a four post mandrel), the rounded tips of the vertices of the triangles better fill the untreated spaces and provide for greater coverage of the surface area of the aneurysm. Another advantage of the 'triangular' or non-round loops formed by such shape of a mandrel post is that the resulting loops formed on the non-round post are generally softer and more compliant than round loops. With non-round configurations, the generally straight sections of the loops have a nearly infinite radius and are consequently much more compliant. This may be counterintuitive, but as described earlier, tighter radiused coils (i.e. smaller loops) are stiffer than larger loops. Triangular posts provide for three substantially linear segments on each loop, which are extremely flexible (due to the near infinitely large radius or curvature) and conformable when deployed in the aneurysm. This novel advantage of non-round posts in the current invention is applicable to any mandrel configuration regardless of the number of posts or the geometric orientation of the posts in relationship to each other. For example, if used on a six post mandrel, the posts may be formed as rounded squares (or four sided polygons) since each post is tangent to four adjacent posts.

Another advantage of the invention is that when a primary coil is formed on the mandrel, because each post is tangent to each of the remaining posts, and those remaining three posts are equally separated from each other around the perimeter of the post, each loop can be formed by winding the primary wire with precisely 360 degrees of rotation around the post plus an additional 120 degrees leading to the next post (i.e., one and one third revolutions around each post). At the point where a wind has wrapped around the post three hundred sixty degrees and then another one third of a revolution, the wind is then aligned tangent to an adjacent post, and the winding then transfers to that adjacent post. The winding continues with each post receiving one and one third revolutions of the wire. The winding pattern predictably reverses in direction (clockwise to counter-clockwise or vise-a-versa) onto the immediately wound post and proceeds likewise in a predictable manner, with each successive loop having the same predictable length (one and one third revolutions around each post). With the four post mandrel configuration, the resulting coil advances one post to the next in a repeatable and consistent manner until the primary wind returns to precisely the same starting point on the first post after encircling each of the four posts by precisely one and one third revolutions, with this pattern repeating itself until the chosen length of the coil is reached. Such a formed coil of repeatable, and thus predictable, completed loops advantageously produces a framing coil that has a strong tendency to assume a spheroid shape, and thus is adaptable to frame generally spherical aneurysms.

In another embodiment of the present invention, the wind may encircle each post of a four post mandrel with a partial revolution, specifically ⅔ of a revolution (240 degrees) before tangentially transferring to the next adjacent post and proceeding accordingly as described above however with successive partial loops. Partial loops are less robust in adhering to it formed shape as complete coils, and a series of partial loops will be more adaptable to conform to irregular shapes as with a correspondingly formed coil with completed loops. Such a formed coil of repeatable, partial revolutions advantageously produces a filling coil that has a tendency to also assume a generally spheroid shape, but is considerably more flexible and thus adaptable to framing irregular shaped aneurysms like multi-lobular or fusiform aneurysms and also more adaptable as a subsequent filling coil in any aneurysm.

In another embodiment of the present invention, a unique coil that serves as both a framing and then filling coil may be produced by wrapping some number of posts of the mandrel first with 240° loops (creating a series of filling loops) and then forming the aneurysm frame by wrapping generally at least four subsequent posts by 480° to create a series of framing loops. The framing portion of the coil is typically deployed first on the catheter in the case of such combination coils so that the aneurism is first framed with the robust full loops and then filled with the softer partial loops.

With embolic coils, the first loop and the last loop may advantageously be of a smaller diameter than the other loops of the coil so that the leading tip of the first coil curls inward (away from the aneurism sack) and thereby presents a lower risk of aneurysm puncture. Another novel feature of the present invention provides in one embodiment where the frustoconical mandrel includes a groove on at least one of the posts at its base so that a first loop wrapped inside the groove has a smaller diameter compared to other loops wrapped outside the groove. The groove may be sized so that as the first loop of the coil is wrapped inside the groove, the depth and width of the groove is filled by the loop of coil. With the groove filled completely by the first loop, any subsequently wrapped loops on this post will either simply lay upon the top of the first loop (typically corresponding to the original post diameter since the previous loop filled the groove) or it can be placed on the mandrel post and will correspondingly have a larger diameter equal to the diameter of the post.

Moreover, it is also desirable for the last loop of an embolic coil to be of a smaller diameter than the other loops of the coil so that the tighter radius of the last loop is a bit stiffer and therefore has an improved chance of retracting away from the deployment catheter and up into the coil mass, rather than possibly project partially into the parent vessel. Another feature of the present invention is an embodiment where the last loop of the coil is of a smaller diameter as compared to its preceding loops. This aspect of the invention is achieved by providing a reduced diameter (or groove) at the upper aspect of the post for which the last loop is formed. This reduced diameter portion of the post provides a location on the post where the last loop is formed into the groove and thus forms a loop of smaller diameter than the preceding loops.

These and other benefits of the invention will best be understood with reference to the accompanying drawings and the detailed description of the invention below.

DETAILED DESCRIPTION OF THE PREFERRED EMBODIMENTS

Figure 1:
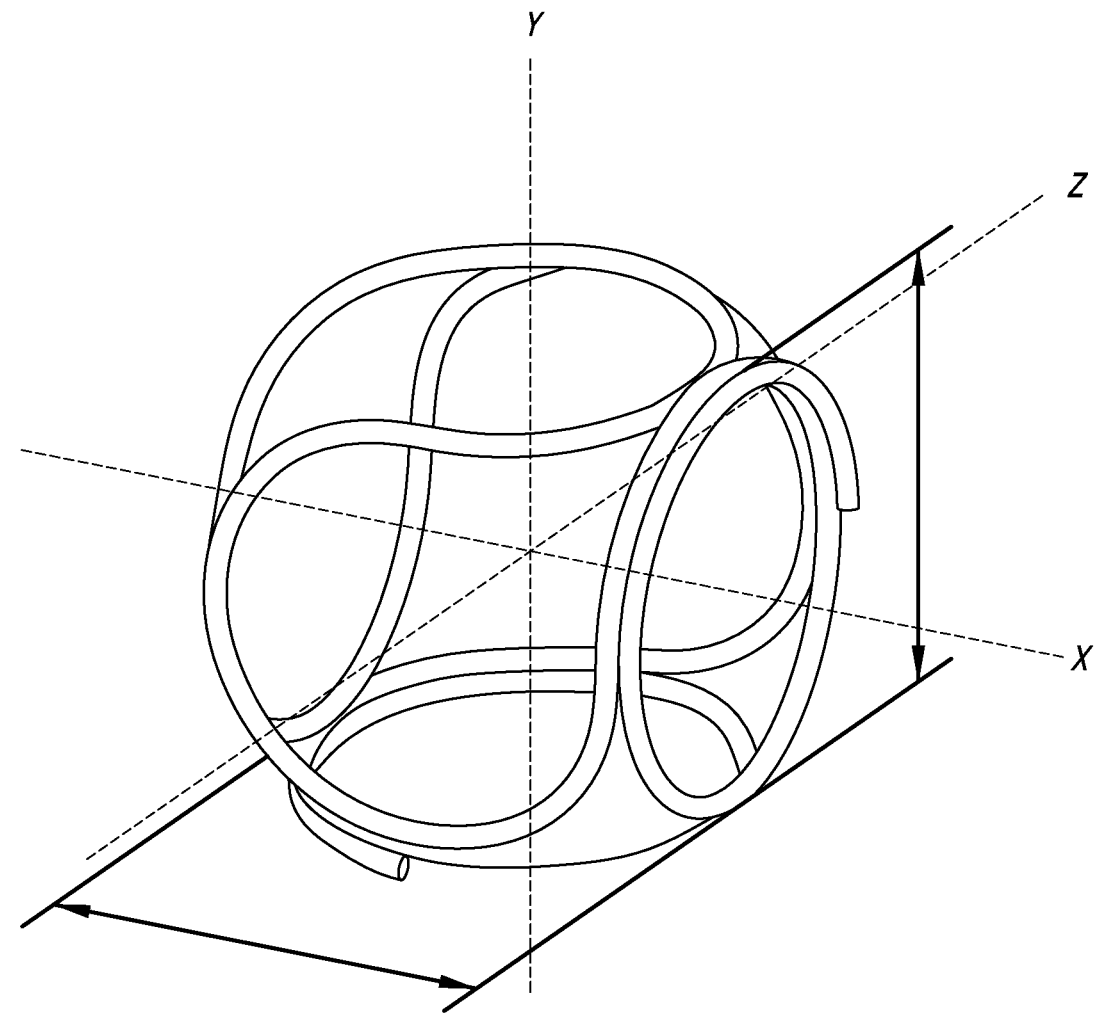
FIG. 1 is an elevated, perspective view of a prior art embolic coil.

FIG. 1 illustrates an embolic coil of the prior art having loops that are formed by a six post mandrel, and thus each series of six loops forms a cube-like structure with three pairs of parallel faces, and the center of the loops fall on the X, Y, and Z axes of a cartesian coordinate system centered on an origin at the center of the cube. The coil of FIG. 1, due to the small diameters of the loops, is stiffer than desirable and also has the potential to slip out of the aneurism and into the parent vessel to which it is attached. The present invention is intended to improve on the characteristics of the coil of FIG. 1.

Figure 2A:
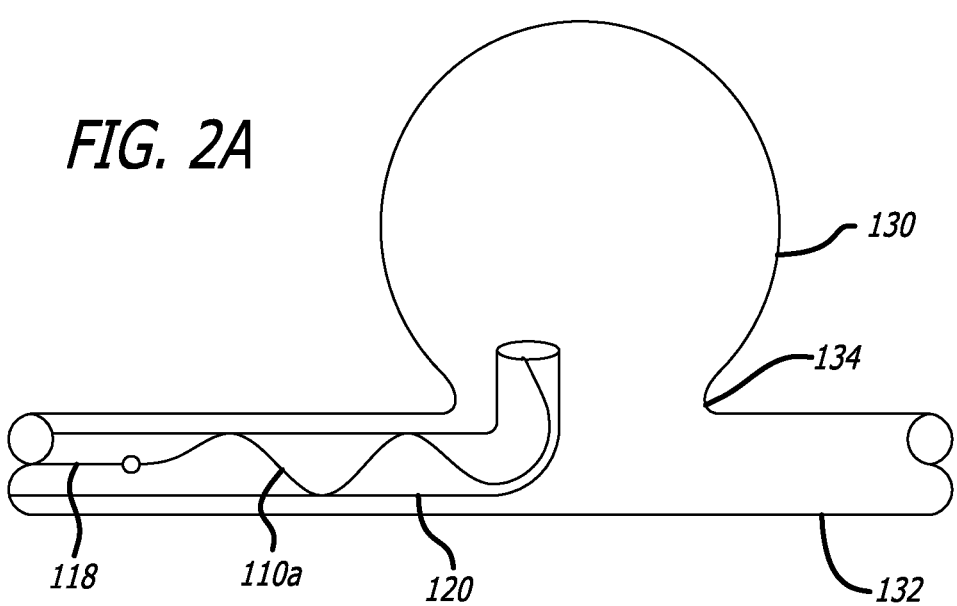
FIG. 2A is a schematic diagram of a catheter delivering an embolic coil of the present invention.
Figure 2B:
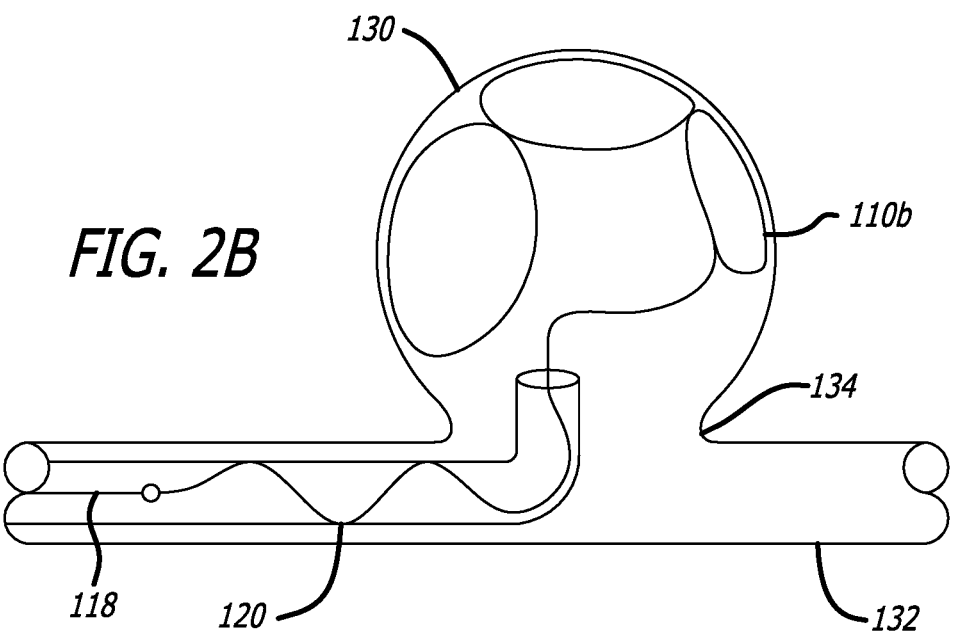
FIG. 2B is a schematic diagram of the coil of FIG. 2A being deployed in an aneurism.

FIGS. 2A and 2B illustrate an example of a deployment of an embolic coil using a coil delivery catheter 120 in accordance with an embodiment. The catheter can be configured to hold and deliver an embolic coil to a designated target location or site for treatment. For example, the frame can be deployed into an aneurysm 130 extending from a primary or parent blood vessel 132. Referring to FIG. 2A, the coil may be delivered in a collapsed or compressed configuration 110*a* in an undeployed state through the catheter 120 to the site of the aneurysm 130. In common use, the elongated coil is pushed through the catheter with a pusher until the coil exits the catheter and deploys into the aneurysm 130 (FIG. 2B). The pusher may comprise a thin wire 118 (often referred to as a pusher wire) for pushing the elongated coil through the catheter. As the coil exits the catheter, it transitions from the elongated configuration 110*a* to the expanded configuration 110*b*, and is allowed to expand within the aneurysm to achieve a completely deployed state. FIG. 2B shows the coil in a partially deployed state as it self-expands within the aneurysm, and the coil would continue to deploy, expand, and fill the aneurism as it is pushed out of the catheter 120 as the coil assumes a spheroidal shape.

After the expanded coil has been separated from the pusher 118, the catheter and/or pusher may be withdrawn from the parent blood vessel, leaving the expanded coil 110*b* in the aneurysm. The coil may be appropriately sized for the aneurysm under treatment, such that the size of the fully expanded frame exceeds the opening or neck 134 from the parent vessel 132 into the aneurysm. This allows the expanded coil to be retained indefinitely within the aneurysm and will not present any loose ends that would extend out of the aneurysm. The expanded coil 110*b* can at least partially fill and stabilize the aneurysm under treatment.

Figure 3:
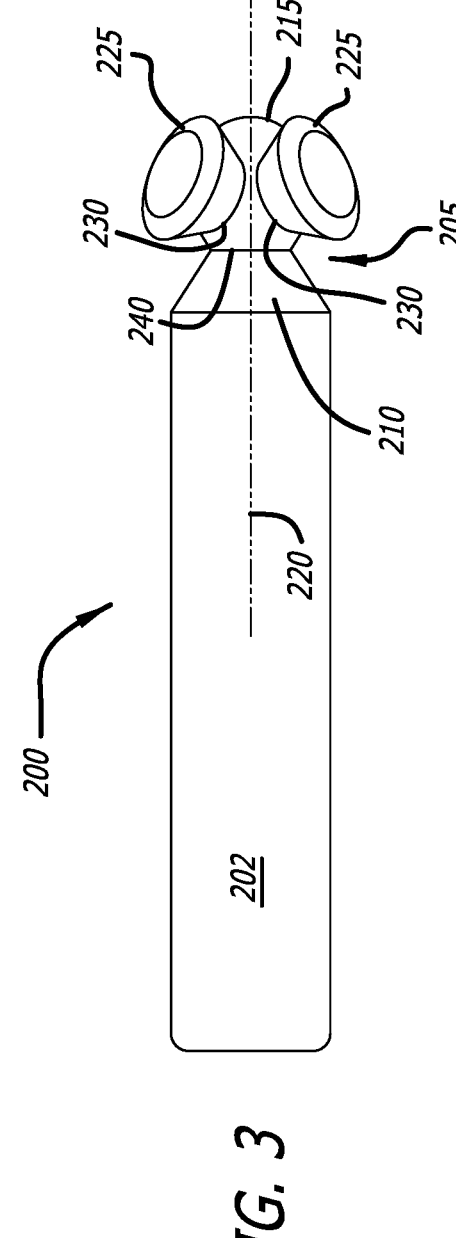
FIG. 3 is a side view of a first embodiment of a mandrel of the present invention.
Figure 4:
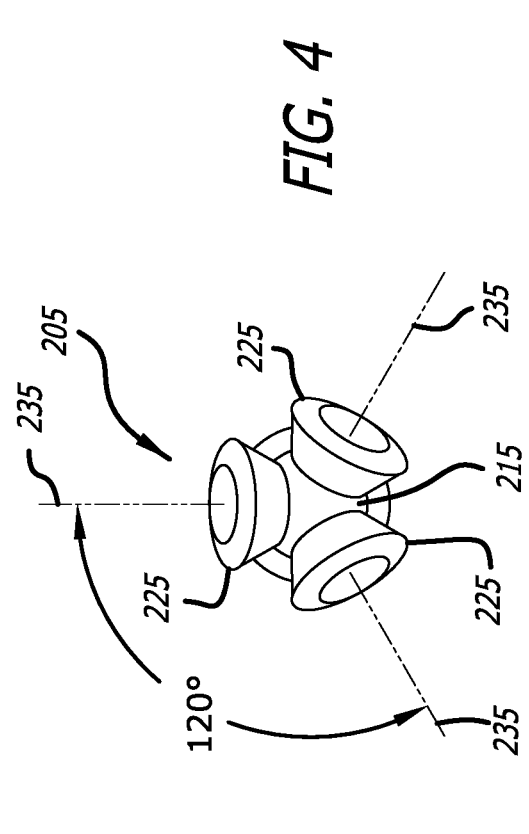
FIG. 4 is an axial top view of the head of the mandrel of FIG. 3 showing the position of the posts.
Figures 8A, 8B:
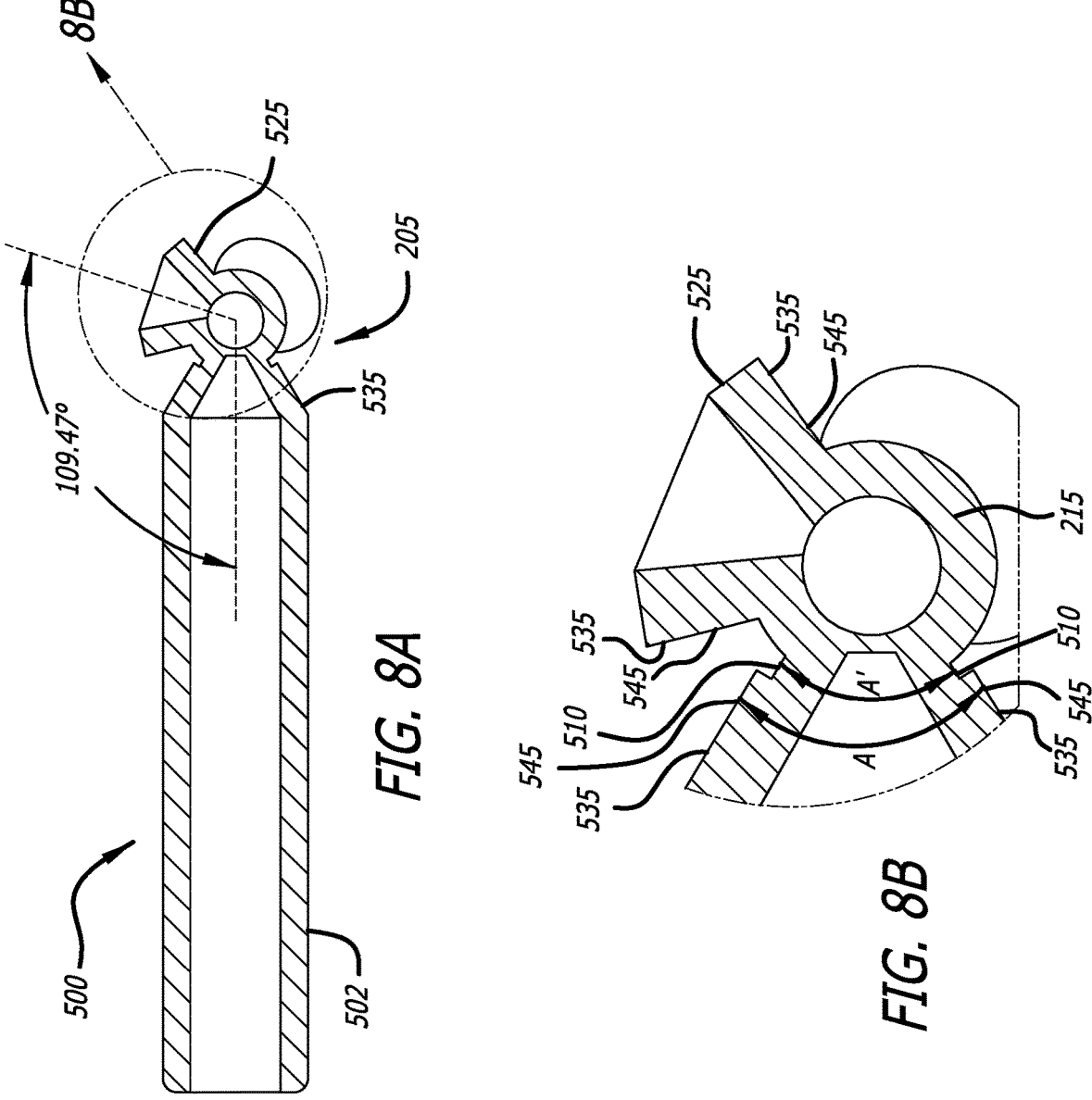
FIG. 8A is a cross sectional view of another embodiment of a mandrel of the present invention.
FIG. 8B is an enlarged, sectional view of the head of the mandrel of FIG. 8A.

FIG. 3 illustrates a mandrel 200 for creating a new embolic coil. The mandrel 200 comprises a cylindrical body 202 (which functions as a handle during use) and a head 205 attached to the body 202. The head 205 of the mandrel 200 includes a tapered end section 210 mounting a spherical base 215 having a center located on the longitudinal axis 220 of the cylindrical body 202. Emanating radially from the spherical base 215 are three posts 225. Each post 225 in a first embodiment is frustoconical with an increasing diameter as the post extends away from the spherical hub 215. Likewise, the tapered end section 210 of the body 202 is formed as a frustoconical surface that is shaped analogously to the other three posts 225. These four projections (posts 225 and tapered section 210) have circular cross sections about their respective longitudinal axis 235, 220 (see FIGS. 3 and 4) passing through the center of the spherical base 215. The intersections 230 of the posts with the spherical base form circles having the same diameter as the intersection 240 of the tapered end section 210 with the spherical base 215. These circles of intersection between the posts and spherical hub, and the tapered end section 210 with the spherical base are each equidistant from the center of the spherical hub, and the longitudinal axes 235 and the longitudinal axis 220 all form angles of one hundred twenty degrees with each other when viewed axially to the handle 202 (FIG. 4) and each forms the tetrahedron vertex-center-vertex angle of approximately 109.47 degrees when viewed longitudinally (FIG. 8A).

Figure 5A:
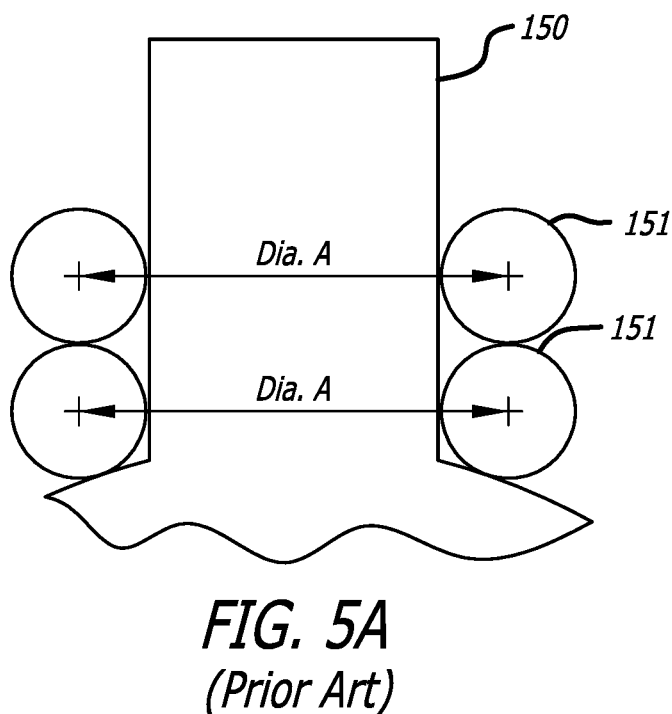
FIG. 5A is a cross sectional view of a cylindrical post of the prior art with multiple windings.
Figure 5B:
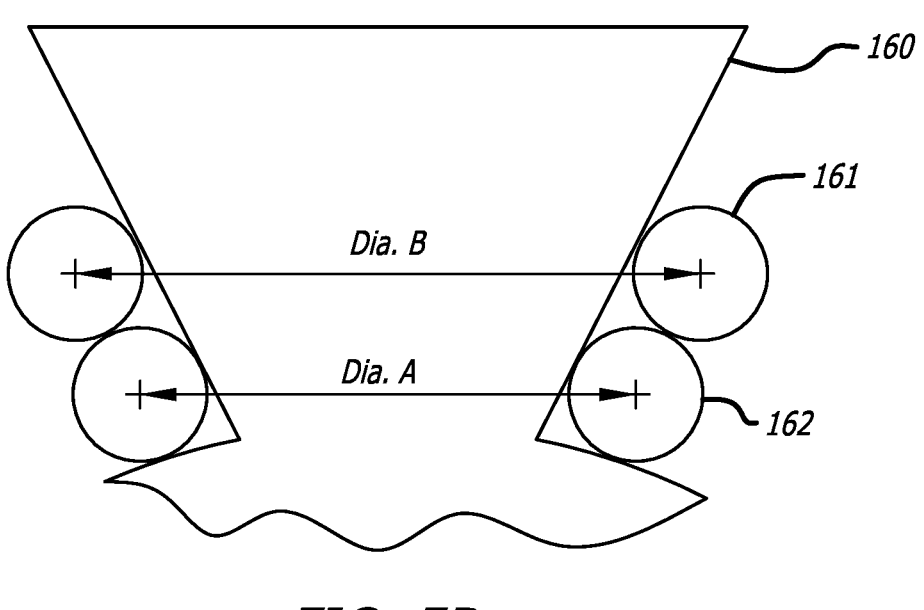
FIG. 5B is a cross sectional view of a first embodiment of a post on the mandrel of the present invention with multiple windings.

FIG. 5A shows a cross sectional view of a cylindrical post 150 of the prior art mandrel with two loops 151 of a coil encircling the post 150. As shown, the diameter A (and consequently the circumference) of the loop formed outwardly from the base is the same diameter A as the inner loop. FIG. 5B shows a cross sectional view of a frustoconical post 160 of the present invention mandrel with two loops 161,162 of a coil encircling the post 160. Due to the tapered shape of the post 160, as shown, any loop formed upon a previous loop will advantageously have a larger diameter B than the loop formed previously on the same post with diameter A.

Figure 6:
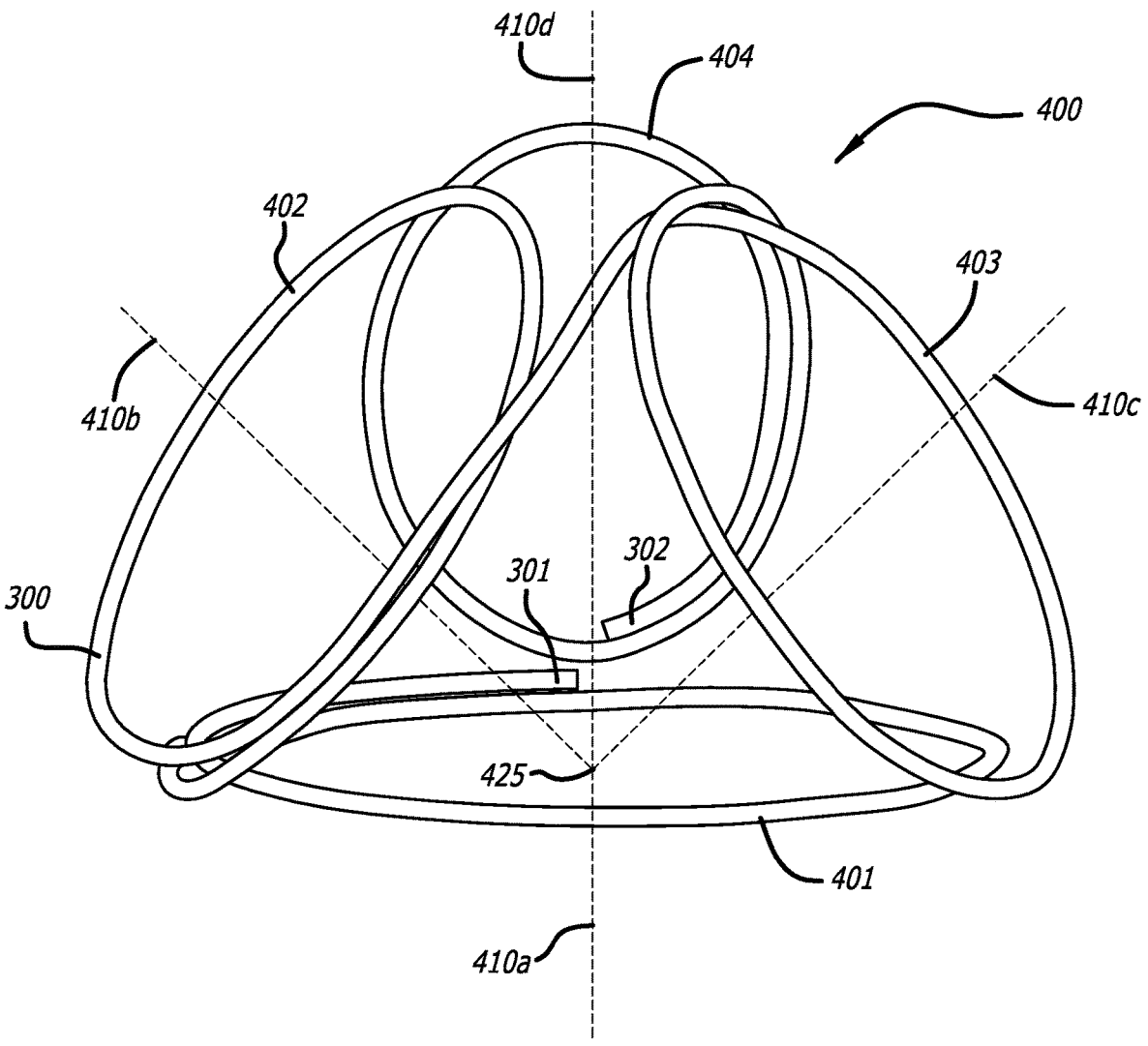
FIG. 6 is an elevated, perspective view of a simple geometric representation of the orientation of loops formed by the winding about the mandrel posts of FIGS. 3 and 4.

A schematic diagram of a resulting coil that is formed about the mandrel (and subsequently removed), is shown in FIG. 6. To create the coil as shown, the winding of a primary wind of a wire 300 is started at point 301 and encircles the first frustoconical post (not shown) with axis 410*a* with 1⅓ revolutions and then winding proceeds to the adjacent post (not shown) with axis 410*b* and then proceeds likewise with 1⅓ revolutions around the posts with axis 410*b*, 410*c* and 410*d* sequentially ending at point 302 to produce the first layer of four loops of the embodied coil. If the desired length of the embolic coil exceeds the length necessary to encircle the first four posts, the next series of loops would be formed outwardly on each successive post on top on the existing loop(s) as shown in partial cross section in FIG. 5B, with resulting larger diameters and circumferences co-axial to the existing loop on the post. The resulting embolic coil has loops that are larger in diameter than the loops of the coil of FIG. 1 for a given aneurism diameter, making it more flexible while at the same time more stable in the aneurism since it is less likely to escape the neck of the aneurism. Additionally, due to the frustoconical shape of each of the four posts, each successively wrapped layer of loops has a greater diameter than the previously wrapped loops to provide for better nesting of the smaller loops into the larger loops of the coil when deployed in the reverse manner to which they were wrapped on the mandrel, as previously described.

Regardless of the coil length, the defining size of the coil (the size of the aneurysm it is intended to be inserted as a framing coil), is defined by the spherical diameter of the outer surface of the last series of loops so created on the mandrel. Specifically, the defining radius is the distance from the center of the mandrel's spherical base 215 to the outer surface of the last loops while on the mandrel. This ensures that the spherical shape of the coil does not exceed the diameter of the aneurysm. Another advantage of the frustoconical posts is that while winding the primary strand onto the posts, the taper assists the primary wind in positioning the initial loop(s) down on the smallest diameter at the spherical base, or snugly against the outer surface of the spherical base or on top of any previously wrapped loops.

Figures 7A, 7B:
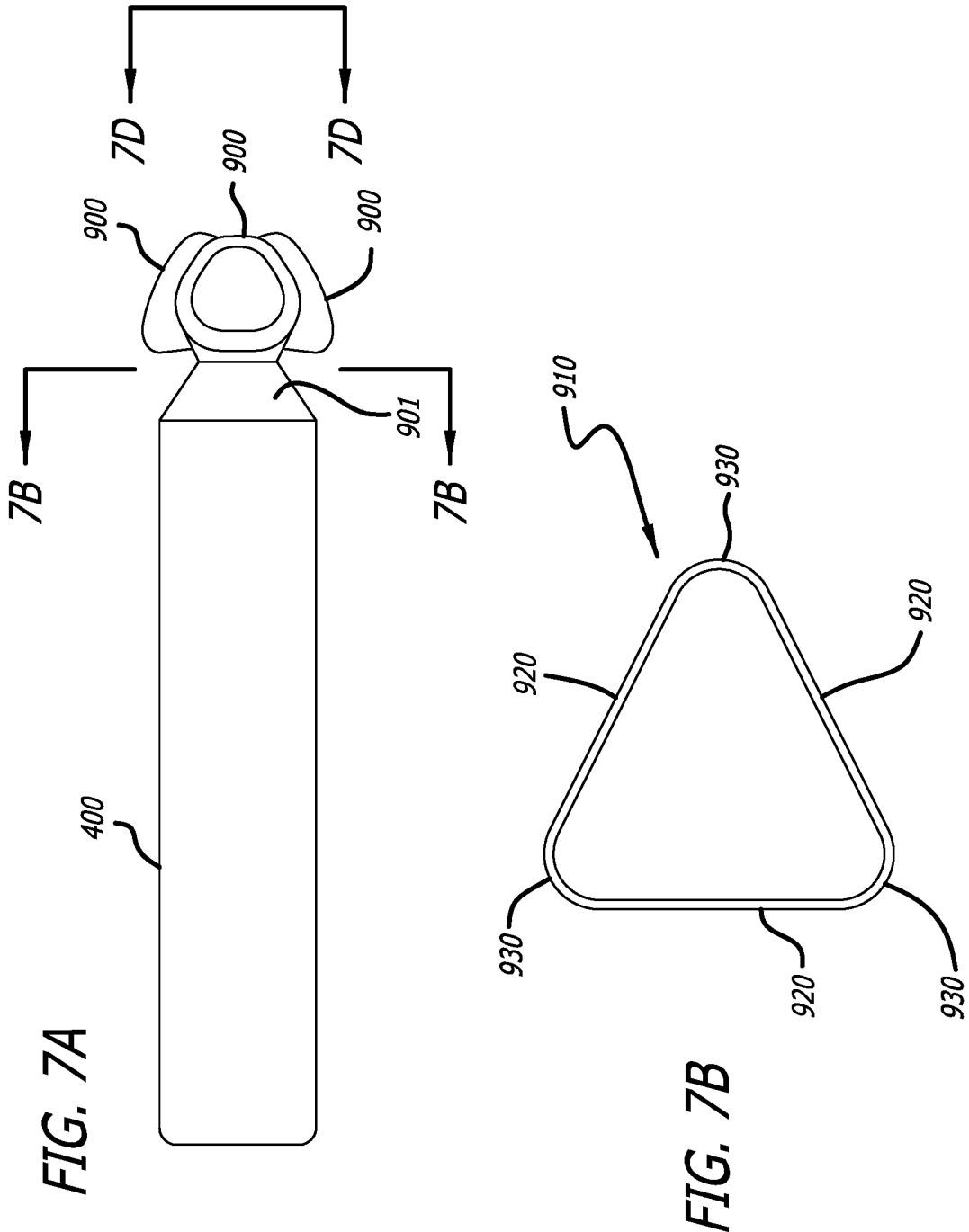
FIG. 7A is a side view of a second embodiment of the present invention.
FIG. 7B is a cross sectional view of the embodiment of FIG. 7A taken along lines 7B-7B.
Figure 7C:
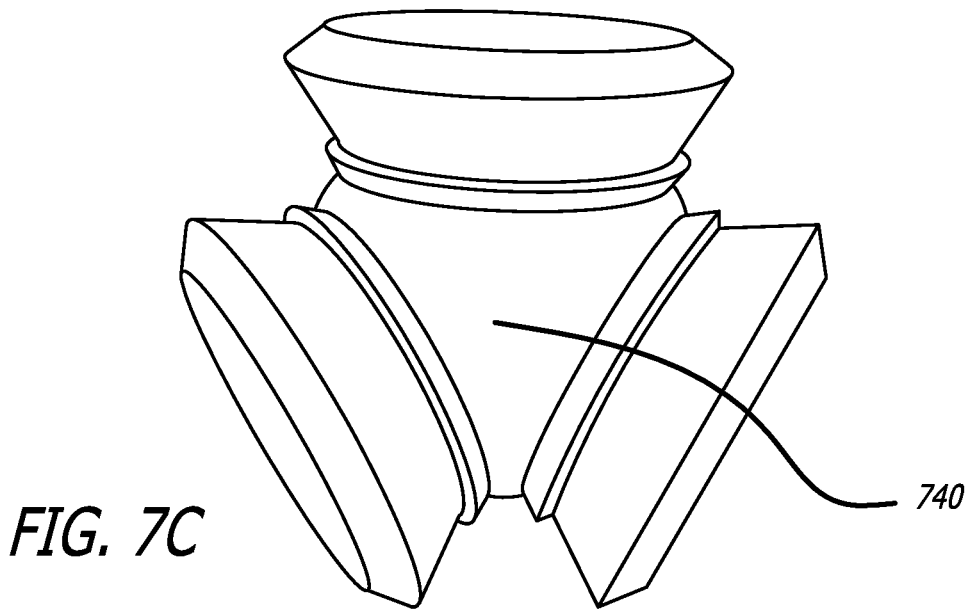
FIG. 7C is an axial top view of the head of the mandrel of FIG. 3.

In another unique and independent advantage of the present invention, the projected posts are not circular in cross-section. With an advantageous four-post configuration, the loop diameters are larger than with a correspondingly sized six-post mandrel. With fewer but larger loops, a greater surface area exists between the adjacent loops. This potentially creates a greater area of untreated aneurysm dome (without loop protection) in the areas at the nodes between the adjacent loops. FIG. 7A illustrates a mandrel 400 having posts 900 and base post 901 with a rounded triangular shape rather than a circular cross section. When configured as such, the mandrel posts 900, 901 (and consequently the coil loops that are formed) have a cross section that is triangle shaped with linear portions and rounded apices. FIG. 7B shows coil loops 910 produced by encircling these triangular posts 900 and 901, and these loops 910 are longer and larger in circumference than loops with circular posts, with linear portions 920 and non-linear portions 930. As described, with a four-post mandrel, the tips of the each adjacent three triangular posts better fill in the four untreated spaces formed by round posts, thereby giving the aneurysm surface more support. FIG. 7*c* illustrates the untreated space

Figure 7D:
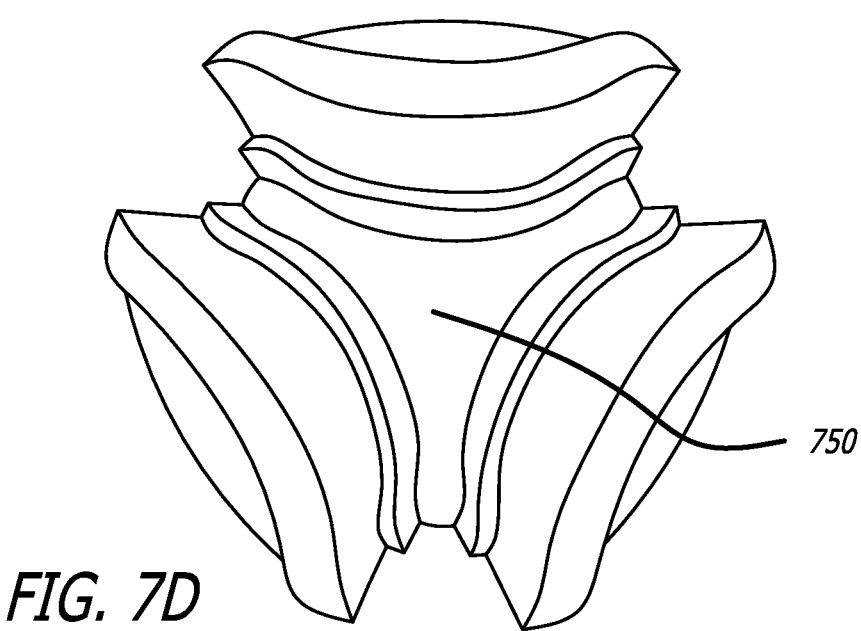
FIG. 7D is an axial top view of the head of the mandrel of FIG. 7A.

740 between three adjacent posts of a four-post mandrel with round posts, while FIG. 7D shows the smaller untreated space 750 between three adjacent posts of a four-post mandrel with rounded-apex triangular posts. Likewise, with the longer loops and greater surface area coverage, these unique coils are likely to lead to higher packing densities (more coil volume deployed into a given aneurysm volume). Additionally, with a six post configuration mandrel, the corresponding non-rounded posts could be configured as a rounded-corner squares (four sided polyhedron) configuration to fill in the spaces between the adjacent four posts. Both of these unique features of the present invention are highly desirable in the field of neurovascular treatment of aneurysms.

It is known in the art that with a given wire (or primary wind coils) size, tighter wound loops or coils diameters (smaller diameter) are stiffer than with larger diameter loops. This becomes very apparent with coils shaped to secondary sizes for very small aneurysms (i.e. less than about 3 mm in diameter). It is not apparent, but another distinct and unique advantage of the non-round post configuration of the present invention depicted in FIG. 7 is that the coil loops so formed, have sections of lower stiffness along the generally straight sections 920 of the coil loops providing for a coil configuration with much greater flexibility than with conventional round posts.

Figure 8C:
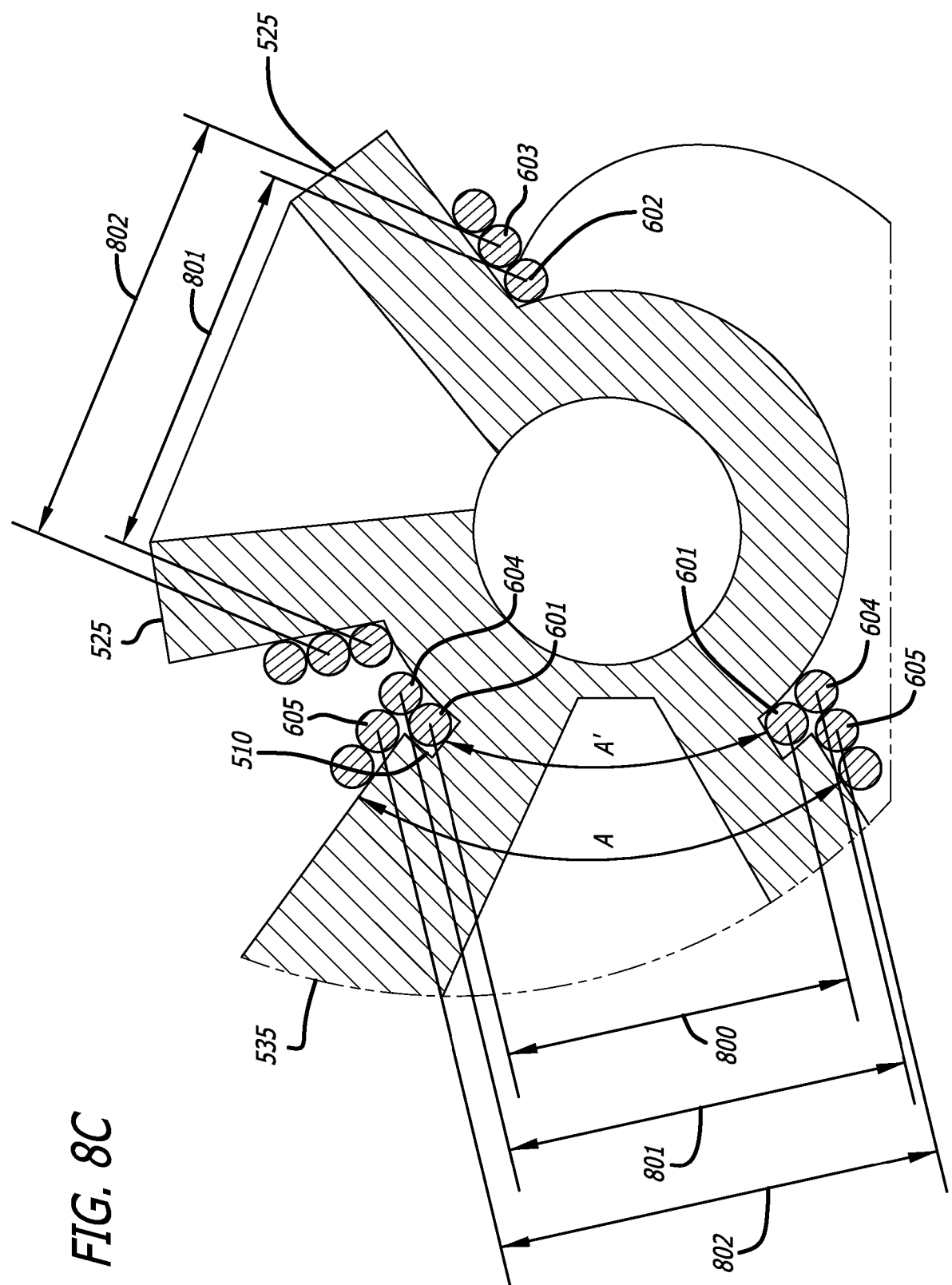
FIG. 8C is an enlarged, sectional view of the head of the mandrel of FIG. 8B with wires wrapped around the posts.

FIG. 8A shows an additional and optional embodiment of the mandrel 500 of the present invention. FIG. 8A illustrates an axial cross section of the mandrel with cylindrical body 502 and frustoconical posts 525 and frustoconical tapered end 535 that is similar in most respects to the posts previously described. However, to create a sometimes desirable smaller diameter loop, a groove 510 is formed at the intersection of the sphere 215 and the exterior surface of the tapered end 535, such that the first wound loop 601 of wire would fill and occupy the groove 510 (FIG. 8C) when the wire wraps around the post in the groove. The arrow A' reflects a diminished loop circumference when compared with the loop formed using the natural surface 545 of post 535 along arrow A. The groove 510 may be used to produce a coil with an initial smaller diameter first loop to produce an advantageous coil with a smaller first loop that protects the tissue in the aneurism as the coil is initially being inserted in place by directing the first deployed loop inwardly to the aneurysm. The groove 510 may alternatively be used to produce a coil with a latter deployed smaller diameter last loop to produce an advantageous coil since the reduced diameter of the resulting last loop has a greater propensity to retract back into the aneurysm sack when the coil is detached from the pusher wire. As shown in FIGS. 8B and 8C, the diameter of loop 604, denoted 801, is equal to the diameter of loop 602, also denoted 801 by winding the wire around the surface 545 at the most proximal location to the sphere 215. Subsequent loop 603 is equal in diameter 802 to loop 605, also denoted 802. Loop 601 occupying the groove 510 has the smallest diameter 800.

Figure 9A:
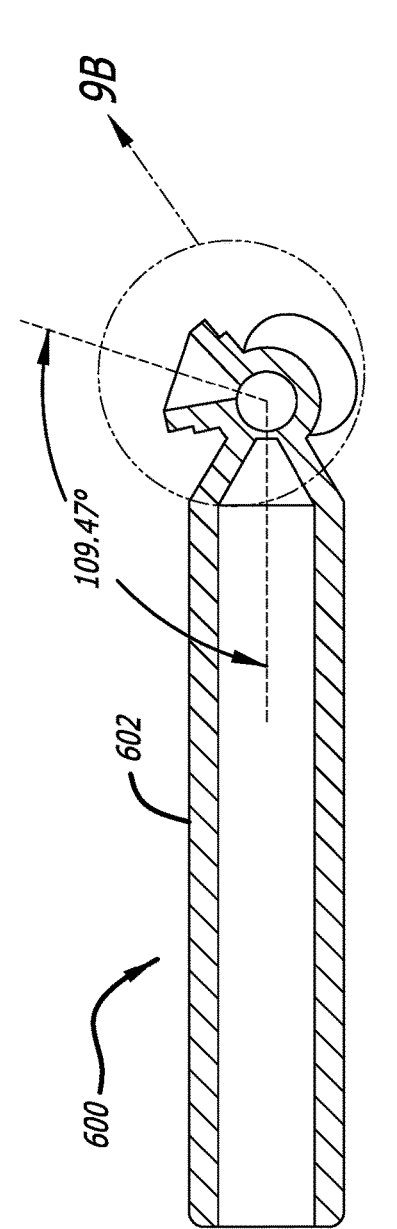
FIG. 9A is a cross sectional view of another embodiment of a mandrel of the present invention.
Figure 9C:
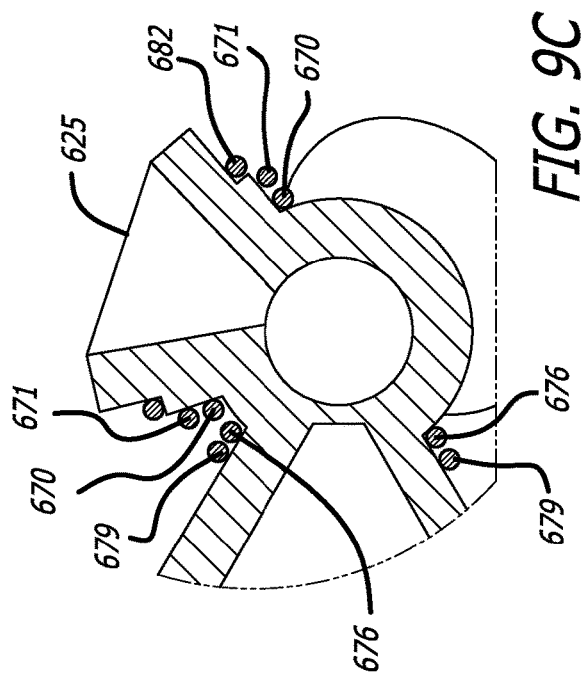
FIG. 9C is an enlarged, sectional view of the head of the mandrel of FIG. 9B with wires wrapped around the posts.
Figure 9B:
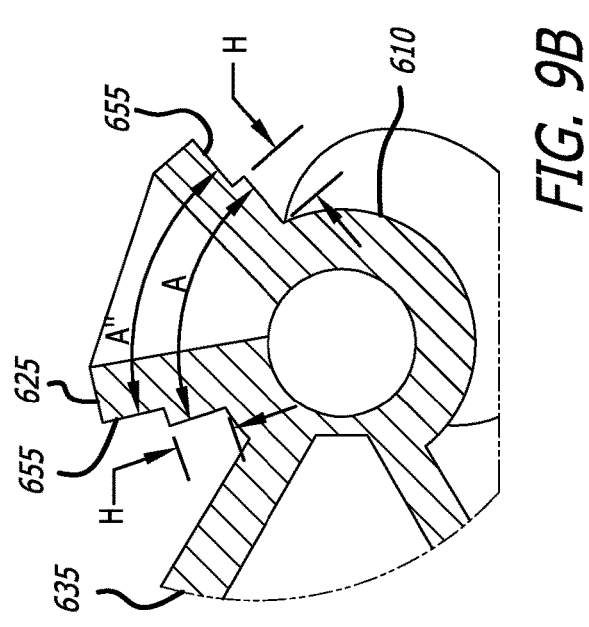
FIG. 9B is an enlarged, sectional view of the head of the mandrel of FIG. 9A.

FIG. 9 shows yet an additional and optional embodiment of the mandrel 600 of the present invention having cylindrical body 602. As shown in FIG. 9A, one or more of the four posts 625 (and/or tapered end 635) has a reduced diameter 655 on the outer circumference of the post at a specified distance H from the spherical base surface 610 (FIG. 9B). This reduced circumference section 655 may be used so as to create a reduced circumference loop (or loops) when the primary wire is wrapped upon it. As described above, the reduced diameter section 655 of the post 625 may be used to produce loops on a coil produce an initial smaller diameter first loop that protects the tissue in the aneurism as the coil is being inserted in place or a smaller diameter last loop of the coil that is advantageous for assisting the last loop to retract within the aneurysm when detached depending on the direction in which the resulting coil in introduced into the aneurysm. When combined with the advantageous groove 510 on the first post (as previously defined), the reduced diameter sections of groove 510 and on the aspect of the post at 655, may be combined to produce a coil with both smaller first and last loops. It should be fully understood, that the benefits of the reduced diameter outer section of the post could also be achieved by use of a groove that is appropriately displaced outwardly on the post.

Additionally, the reduced circumference portions of the posts may be used to form an entire series of reduced diameter loops if the frustoconical taper of the post is not sufficient to produce enough desired reduction in circumference as comparison to the loops formed on the natural surface of the posts. As shown in FIG. 9C, loops 670 and 676 have a common loop diameter shown by arrow A and subsequent loops 671 and 679 have slightly larger diameter loops as a result of the frustoconical post shape. However, loop 682 occupying reduced section 655 has a smaller diameter loop corresponding to arrow A" as a result of the modified width of the post 625 at the distal region. Loop 682 can be made as small as desired by forming the recess 655 on the post, producing a coil with the benefits discussed above. These described advantages of the smaller loops formed by the groove 510 and/or reduced diameter portions 655 of the projecting posts, are not specifically applicable only to a 4-post mandrel design, and may be applicable to any mandrel with any number of posts and any post cross-sectional geometry. Additionally, the reduced diameter sections may have a different cross sectional geometry than this parent post. Moreover, it is understood that the groove and reduced diameter portions can be used in combination to create a coil with both initial and final smaller loops.

In another embodied advantage of the present invention, the base diameter of the posts are not tangent to each other but rather slightly spaced apart such that when the primary wind is wrapped around the post, it lays flat at the base of the base sphere and also leaves room for the successive loop around the adjacent post to have room for the next loop. That is, the posts are displaced (by reducing their diameter) from each other by approximal twice the diameter of the coil spring that defines the primary wind. This feature reduces the undesirable 'bump' in the coil as it transitions from one post to the next because the coil primary wind does not have to cross over a previously formed loop in the coil when it is transitioned to the next adjacent post.

While certain embodiments, variations, and advantages of the present invention have been described and depicted, it is to be understood that the invention is not limited only to those descriptions and depictions. A person of ordinary skill in the art will readily recognize many substitutions, modifications, and alterations to the above-described embodiments, and the scope of the present invention is intended to include all such substitutions, modifications, and alterations.

I claim:

1. An embolic coil for intravascular treatment formed from a wire, and when deployed comprises:

multiple non-parallel faces with each face formed by multiple layers of loops of the wire, the multiple layers of loops of each face including a first loop of a first layer and a second loop of a second layer, each of the first and second loops comprising linear elements connected by non-linear elements.

2. The embolic coil of claim 1, wherein each of the first and second loops is a substantially triangular loop.

3. The embolic coil of claim 1, wherein the first loop has a first circumference different than a second circumference of the second loop.

4. The embolic coil of claim 1, wherein the first loop precedes the second loop and has a first circumference larger than a second circumference of the second loop.

5. The embolic coil of claim 1, wherein all of the multiple layers of loops of each face comprises linear segments connected by non-linear segments.

6. The embolic coil of claim 1, wherein each of the multiple layers of loops of each face is a substantially triangular loop.

7. An embolic coil for intravascular treatment formed from a wire and when deployed comprises: multiple non-parallel faces that are each formed by a single substantially triangular loop comprising linear segments connected by non-linear segments.

* * * * *